United States Patent [19]
Adler et al.

[11] Patent Number: 5,419,624
[45] Date of Patent: May 30, 1995

[54] ARRANGEMENT FOR DETECTING A CRITICAL DRIVING TORQUE IN A MOTOR VEHICLE

[75] Inventors: Uwe Adler, Schweinfurt; Hans-Jürgen Drexl, Schonungen; Dieter Lutz, Schweinfurt; Franz Nagler, Ottendorf; Martin Ochs; Stefan Schiebold, both of Schweinfurt; Hans-Joachim Schmidt-Brücken, Geldersheim; Wolfgang Thieler, Hassfurt; Michael Wagner, Niederwerrn; Holger Westendorf, Hambach; Rainer Wychnanek, Madenhausen, all of Germany

[73] Assignee: Mannesmann Aktiengesellschaft, Dusseldorf, Germany

[21] Appl. No.: 211,961

[22] Filed: Apr. 21, 1994

[30] Foreign Application Priority Data

Oct. 22, 1991 [DE] Germany .................. 41 34 831.1

[51] Int. Cl.$^6$ .................. B60T 8/32; B60K 28/16; G05D 17/00; G01M 17/06
[52] U.S. Cl. .................. 303/112; 180/197; 188/181 T; 303/100
[58] Field of Search ............... 303/112, 100, 103, 104, 303/95, 111, 102, 106–110; 188/181 T; 364/426.01, 426.02, 426.03; 180/197, 65.4; 318/139; 73/9

[56] References Cited

U.S. PATENT DOCUMENTS 5,135,290 8/1992 Cao .................. 303/112

FOREIGN PATENT DOCUMENTS 0227003 7/1987 European Pat. Off. .
3531653 3/1987 Germany .
8910863 11/1989 WIPO .
9115378 10/1991 WIPO .
9115386 10/1991 WIPO .

*Primary Examiner*—Douglas C. Butler
*Attorney, Agent, or Firm*—Cohen, Pontani, Lieberman, Pavane

[57] ABSTRACT

An apparatus for determining a critical driving torque and information representing the coefficient of friction at the wheel grip limit for a vehicle having a plurality of driven wheels. It is suggested that torque control devices be assigned to at least two of the driven wheels so that the ratio of the driving torques of the two driven wheels can be varied, wherein torque sensing device generate a torque signal corresponding to the magnitude of at least the greater of the driving torques of the driven wheels. A wheel slip sensing device is associated with the driven wheels and detects an increase in the slip of the wheel with the greater driving torque beyond a predetermined limit. The information on the coefficient of friction is generated depending on the magnitude of the detected driving torque of the wheel whose slip exceeds the limit. To determine the information concerning the coefficient of friction, the distribution of driving torque between the front axle and rear axle is periodically increased in an alternating manner.

18 Claims, 1 Drawing Sheet

ARRANGEMENT FOR DETECTING A CRITICAL DRIVING TORQUE IN A MOTOR VEHICLE

FIELD OF THE INVENTION

The invention is directed to an arrangement for determining information representing a critical torque in the wheel grip limit range for a motor vehicle having a plurality of driven wheels.

BACKGROUND OF THE INVENTION

Conventional antilock braking systems (ABS) and drive slip regulating systems (ASR) are designed to regulate on the basis of a fixed coefficient of friction between the wheel and the road surface, usually the coefficient of friction for a dry road with good gripping properties. Corresponding to the coefficient of friction is a (critical) wheel load-dependent driving torque which can still be transmitted to the road surface without exceeding a permissible slip limit, i.e. without spinning of the driving wheel. A change in the coefficient of friction, e.g. due to wet or icy road surfaces, can lead to an impairment of the regulating characteristics. In antilock braking systems, for example, such a change in coefficient of friction can result in a lengthening of the braking distance on slick icy roads. Therefore, it is desirable to adapt the regulating characteristics of such systems to the state of the road being traveled at the time.

In a regulating system for antilock braking systems and drive slip regulating systems known from DE 38 14 956 A1, the current coefficient of friction and the slope of the slip curve are calculated from the transmitted driving torque or braking torque and the rotating speed of a driving wheel. Thus, there is no exact determination of the coefficient of friction.

SUMMARY OF THE INVENTION

The object of the present invention is to provide an arrangement which makes possible an exact determination of quantified information representing a critical driving torque in the wheel grip limit range while the motor vehicle is in driving operation. The required cost on apparatus for this purpose is kept as low as possible.

This object is met, according to the invention, in an arrangement of the generic type by means of an apparatus for determining information representing a critical driving torque at a driving wheel of a motor vehicle having a plurality of driving wheels comprising: driving torque sensors for determining driving torque information corresponding to the magnitude of the respective driving torque of the respective driving wheel, speed sensors for determining speed information corresponding to the magnitude of the respective speed of the respective driving wheel, a computation circuit for determining and supplying information on the critical driving torque, electrical motors for individually driving the driving wheels, and torque control devices for separately controlling the electric motors.

The computation circuit comprises means for:

(a) causing at least at one of the driving wheels, a temporary increase in driving torque a predetermined quantity beyond that of the other driving wheels, wherein the predetermined quantity is a predetermined fixed amount or a predetermined percentage of the current driving torque of this driving wheel;

(b) comparing speed information determined from the driving wheel with increased driving torque by its respective speed sensor with the speed information determined from at least one of the other driving wheels, which have a relatively lower driving torque, by its respective speed sensor for the purpose of detecting slip;

(c) performing a step when the computation circuit determines a speed differential not exceeding a given permissible relative speed differential wherein a wheel grip limit is not exceeded, of either (i) transmitting a signal with the information that the temporarily increased driving torque is not critical or (ii) causing the driving torque to be increased again by a greater amount;

(d) transmitting a signal representing the critical driving torque when the given permissible relative speed differential is determined by the computation circuit; and (e) determining the critical driving torque, when the computation circuit determines a speed differential exceeding the given permissible relative speed differential wherein the wheel grip limit is exceeded, and transmitting the critical driving torque as a signal for the purpose of iterative approximation to the permissible relative speed differential by repeated temporary increases in the driving torque wherein at least the first of the repeated increases is smaller than its respectively preceding temporary increase in the driving torque.

The invention may further be characterized in that the computation circuit keeps the sum of all driving torques of the motor vehicle at a predetermined value via the torque control device during the temporary increase in the driving torque of at least one driving wheel.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
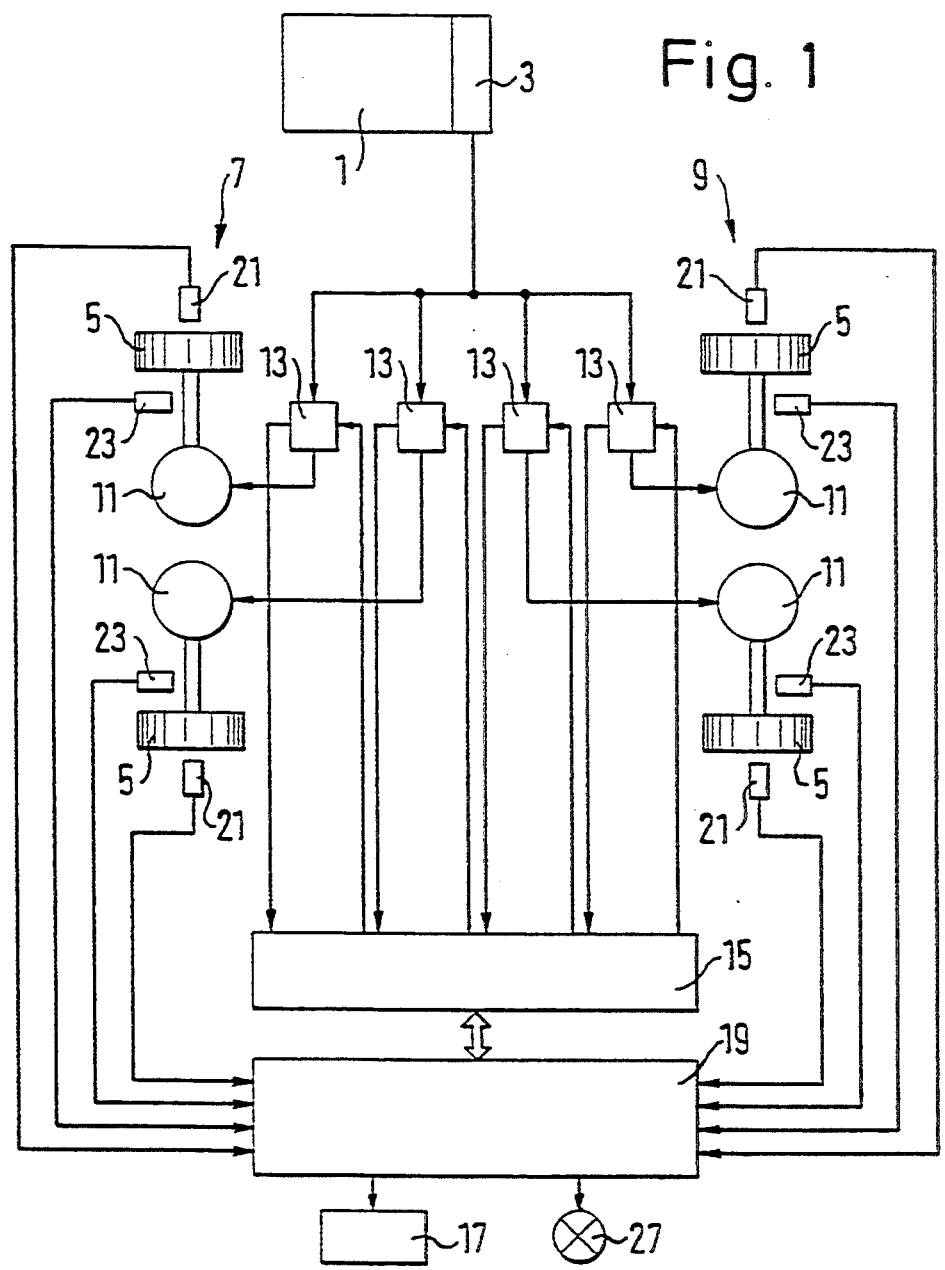
FIG. 1 shows a schematic view of a drive arrangement for a motor vehicle having an arrangement for determining information representing the coefficient of friction at the wheel grip limit.

The invention is based on the idea that the critical driving torque value can easily be determined during only a brief, i.e. temporary, increase in driving torque in only some of the driven wheels up to the point where these wheels reach their grip limit, since the motor vehicle is outfitted with individually controlled electric drive motors. The driving torque in question can be calculated by a computation circuit based on the detected power supplied to the electric motors in question and on the detected current wheel rotation speed corresponding to the speed of the electric motor or with the intermediary of a gear unit in a given ratio to the speed of the electric motor. According to the invention, the increase in driving torque is only temporary so that the driver does not perceive any changes in the driving performance. This means that the increase in torque must be proportioned in such a way that there are practically no noticeable outward reactions due to the inertia of the vehicle. This is possible, for example, when the duration of the increase in torque is limited to the time required for a fraction of a revolution of the wheel, preferably a maximum of half a revolution, in particular a maximum of a tenth of a revolution. During the temporary increase in driving torque, the computation circuit carrying out the procedure for determining the critical driving torque compares the wheel speeds of the driving wheels and determines a relative speed differential, i.e. with reference to the wheel rotating speed, which corresponds to the slip differential between the two wheels being compared. Given the standard assumption that the driving wheel with the smaller driving torque does not yet exhibit substantial slippage, the relative speed differential directly represents the absolute slippage of the driving wheel with the temporarily increased driving torque. As long as the determined relative speed differential remains below a given critical limiting value, e.g. in the range of 10% to 15% the driving wheel in question will not yet spin, so that—assuming constant friction ratios—a driving torque in the determined order of magnitude can safely be used in driving operation. The increase in the driving torque initiated by the computation circuit is carried out in a fixed amount or in a given percentage of the actual or current driving torque at the wheel in question. For example, an increase by at most a fourth of the actual driving torque is advantageous. The predetermined amount of increase may also be determined as a function of the wheel speed. The procedure for determining the critical driving torque is repeated at different times at least when the fixed slip limit has not yet been reached by the increase in torque. Information concerning the level of the as yet uncritical driving torque can then be supplied. However, it is also possible to repeat the procedure immediately, in which case a greater increase in driving torque is advisably used so as to approximate the given slip limit and accordingly the critical driving torque.

As soon as the slip limit is exceeded, as detected by means of the determined relative speed differential, the computation circuit attempts to determine the exact value of critical driving torque by applying an iterative process, i.e. the selected amount by which the driving torque is increased is less than that previously selected. For example, if the slip limit is already exceeded by the first increase in torque, the amount of the increase can be halved, for example. If the slip limit is still exceeded by this new increase in torque, an even smaller increase is effected in the next step; if not, a value lying between the last two amounts is selected. In this way, the computation circuit can approximate the actual value of the critical driving torque with sufficient accuracy in a few steps.

When the wheel load is taken into account, the critical driving torque is also a measurement for the current coefficient of friction between the slipping wheel and the road surface. The information obtained in this way concerning the coefficient of friction or, even at this point, the determined value of the critical driving torque can be used to control the regulating characteristics of the antilock braking system and/or the drive slip system and/or to notify the driver, e.g. by means of a warning device or a display showing the quality of the road surface.

The driving torques are advisably varied in such a way that the torque control device maintains the sum of the driving torques of all driven wheels of the motor vehicle at a given value when determining the critical driving torque and/or the coefficient of friction (hereinafter both the critical driving torque and the coefficient of friction are usually included when referring to the determination of the coefficient of friction). The torque control device accordingly changes only the distribution of the driving torques to the driven wheels so that there is no risk of a loss in driving comfort due to changes in torque while determining the coefficient of friction. Further, such negative effects due to the inertia of the motor vehicle mentioned above and the increase in torque which is merely temporary are extensively eliminated by dampening.

Since a variation in the driving torque between wheels of the same driving axle could lead under certain circumstances to noticeable yaw moments around the vertical axis of the motor vehicle, the torque control devices preferably vary the ratio of the sum of the driving torques of the driven wheels of a front axle of the motor vehicle to the sum of the driving torques of the driven wheels of a rear axle.

In order to determine the information concerning the coefficient of friction, it is sufficient in itself to increase and then subsequently reduce the driving torque of one and the same wheel or the wheels of one and the same driving axle. However, to detect differences in the critical driving torques or coefficients of friction between the front axle and rear axle and/or the wheels on the left and right sides of the motor vehicle, the torque control devices advisably increase the driving torques of at least both driven wheels alternately.

Determination of the coefficient of friction between the wheel and road when reaching the grip limit depends not only on the driving torque to be applied for this operating state, but also on the wheel load acting normally to the road surface. This can be assumed as a constant value to a first approximation, at least for a nonaccelerating driving state. But in order to determine the friction of coefficient with increased accuracy the arrangement preferably has wheel load sensing means which detect the magnitude of the wheel load acting on the slipping wheel normally to the road surface at a given moment. The wheel load can be measured, for example, by means of force sensors at the chassis of the motor vehicle or can be taken from other systems regulating the chassis, e.g. shock-absorbing regulating means. The wheel load can also be calculated from information concerning the driving status, e.g. from information on the steering angle as a measurement for a turning radius and/or from information concerning the vehicle acceleration or the roll angle including the values characterizing the inertia of the vehicle, e.g. its mass, roll inertia or pitch inertia.

The information concerning the coefficient of friction and critical driving torque may be updated periodically at given time intervals, e.g. every 10 seconds or once every minute. However, updates may also be carried out depending on the situation, advisably in that a control unit, at given time intervals, detects changes in slippage occurring at driven wheels of a front axle and a rear axle of the motor vehicle during driving operation and initiates an update of the information representing the critical driving torque and the coefficient of friction. This variant makes use of the fact that the wheel slip changes to some extent from the front axle to the rear axle, even during normal driving operation, when the vehicle moves, for example, from a road surface with a high coefficient of friction to a road surface with a lower coefficient of friction. As a rule, the slippage will not change to the extent that the grip limit of the wheels is exceeded; nevertheless, the change in slippage is sufficient to trigger an updating of the friction coefficient information, particularly since it occurs in a determined sequence at the wheels, i.e. first at the front axle and then at the rear axle or vice versa when traveling in reverse.

The invention proves particularly advantageous in motor vehicles in which the individual electric motors, each of which is coupled with an individual driving wheel, are supplied with electrical current via power electronics from a generator arrangement driven by an internal combustion engine. In a drive arrangement of this type, the computation circuit can calculate the magnitude of the driving torque depending on the magnitude of the electrical power supplied to the electric motor of the slipping wheel and on the rotating speed of this wheel. Accordingly, signals which are already available may be used for sensing the torque. An example of such a drive arrangement for a motor vehicle with wheels driven individually by electric motors is described e.g. in DE 4011291 A1. The electric motors are electronically commutated multipolar devices whose rotor is formed by a plurality of permanent magnets of alternating polarity.

In order that the individual stator windings are supplied with current accurately with respect to position, these electric motors are outfitted with devices for determining in a highly precise manner the respective relative position of the rotor and stator and accordingly already from the commencement of operation possess information from which the current or actual speed and changes in speed can be determined very accurately already in the time required for a fraction of a revolution. Thus, there is no longer any need for costly additional devices for this purpose.

Since the actual differences in speed between two wheels arranged on different longitudinal sides of the motor vehicle while making a turn would lead to erroneous information about existing slippage because the cornering geometry alone would require a speed differential even in the absence of slip, a sensor device (e.g. a steering wheel angle pickup or transducer) which senses such cornering is advisably provided. This sensor device can cause the computation circuit to determine the critical driving torque only when driving along a straight line or can compensate for errors due to the different radii of curvature of the track of the wheel in question. However, it is also possible to carry out a speed comparison of only those wheels on the same longitudinal side of the motor vehicle insofar as an approximately identical turning radius may be anticipated for these wheels.

The invention is explained in more detail in the following with reference to the drawing.

FIG. 1 shows an internal combustion engine 1 of a motor vehicle to which is flanged a generator arrangement 3. All wheels 5 of the motor vehicle on its front axle 7 and rear axle 9 are driven separately by electric motors 11, each of which is powered, via a current control circuit 13, by the generator arrangement 3. A control unit 15 controls the current control circuits 13, e.g. depending upon the position of an accelerator pedal, in such a way that a desired driving torque is adjusted at the wheels 5. The output of the generator arrangement 3 and internal combustion engine 1 are also controlled in a manner not shown in more detail depending upon the desired driving torque.

Associated with the drive arrangement are regulating systems, indicated at 17, for an antilock braking system (ABS) of the vehicle brakes and/or a drive slip regulating system (ASR) limiting the slip of the driving wheels. Information about the coefficient of friction of the road surface being driven upon at a given moment is supplied to the regulating systems from a computation circuit 19 so as better to adapt the regulating behavior of these systems to the quality of the road surface at a given moment. The computation circuit 19, which can be a microprocessor or the like and can be a component part of the control unit 15, receives information from the control unit 15 concerning the instantaneous electrical output of the electric motors 11 based on the instantaneous engine voltage times instantaneous engine current. The computation circuit 19 further obtains information representing the instantaneous wheel speed from the sensors 21 and information about the instantaneous wheel load acting normally to the road from sensors 23. The computation circuit 19 calculates the driving torque of the wheel 5 by dividing the electric output of its electric motor 11 by the wheel speed and forms the ratio from the driving torque divided by the wheel load. This ratio represents a measurement for the coefficient of friction at the wheel grip limit when formed for values of the torque and wheel load determined when approaching the grip limit.

Figure 2:
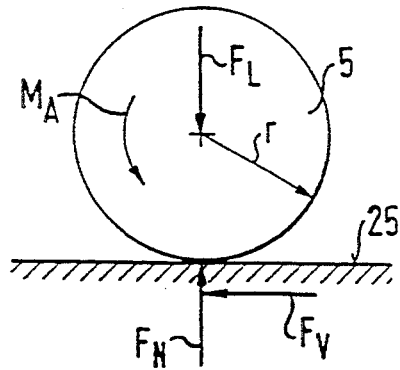
FIGS. 2 and 3 are diagrams illustrating the principle used in determining the coefficient of friction.

FIG. 2 shows the force ratio and torque ratio of a driven wheel 5 traveling on a road 25, where $M_A$ is the driving torque of the electric motor 11, $F_L$ is the wheel load vertical to the road 25, $F_N$ is the normal force at the point of contact of the wheel 5 with the road, $F_V$ is the propulsive force of the wheel 5, r is the dynamic tire radius.

Figure 3:
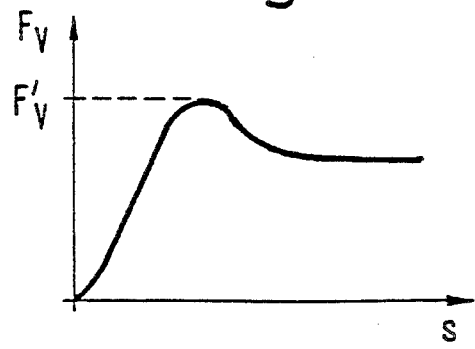

The wheel slip s is equal to the quotient of the difference between the distance actually covered by the wheel 5 and the theoretically traveled distance determined by the circumferential length of the wheel 5 divided by the theoretically traveled distance. The propulsive force $F_V$ is substantially proportional to the wheel slip s at low propulsive force. However, as is shown in FIG. 3, when a limiting propulsive force $F'_V$ is reached, the slip increases very sharply accompanied by a spinning of the wheel 5. The coefficient of friction $\mu$ can be calculated for the limiting propulsive force $F'_V$ based on the following equations. As long as the wheel 5 grips the road, then $$F_V < \mu \cdot F_N \tag{1}$$

However, if the driving torque of the wheel 5 is increased to a value at which the wheel begins to skid, that is, when the limiting propulsive force $F'_V$ is reached, then $$F_V = \mu \cdot F_N \tag{2}$$

Assuming the wheel force $F_L$ equals the normal force $F_N$, then equation (2) and the following equation $$F_V = M_A / r \tag{3}$$

give the following equation for the coefficient of friction $\mu$ when the wheel grip limit is reached:

$$\mu = \frac{M_A/r}{F_L}. \quad (4)$$

In order to determine the coefficient of friction $\mu$, the computation circuit 19 provides for a redistribution of the driving torques between the wheels 5 of the front axle 7 and rear axle 9 via the control unit 15. The driving torques are redistributed in such a way that the sum of the driving torques of all wheels 5 remains constant in order to prevent loss of comfort. The control unit 15 increases the driving torque alternately at the front axle 7 and rear axle 9 as long as the computation circuit 19 determines, on the basis of the speed information supplied by the sensors 21, that the drive slip at the wheels 5 continues to increase as the driving torque increases. In so doing, the computation circuit 19 checks for the wheel slippage over a given limit. If the wheel slip limit has been exceeded, the instantaneous driving torque $M_A$ and the instantaneous wheel load $F_L$ are detected and the coefficient of friction $\mu$ is calculated based on these quantities.

The computation circuit 19 not only supplies information concerning the coefficient of friction to the antilock braking system and/or drive slip regulating system 17, but also notifies the driver of the state of the road surface via a display 27.

The computation circuit 19 initiates a periodically repeated update of the information on the coefficient of friction, e.g. at intervals of approximately 10 seconds or a minute. Further, the speed information from the sensors 21 is also checked for successive changes in slip, first at the front axle 7 and then at the rear axle 9, during driving. Successive changes in slippage at the front axle 7 and rear axle 9 are interpreted as sudden changes in the road quality, whereupon the information on the coefficient of friction is updated.

We claim:

1. An apparatus for determining information representing a critical driving torque at a driving wheel of a motor vehicle having a plurality of driving wheels, comprising: driving torque sensors for determining driving torque information corresponding to the magnitude of the respective driving torque of the respective driving wheel, speed sensors for determining speed information corresponding to the magnitude of the respective speed of the respective driving wheel, a computation circuit for determining and supplying information on the critical driving torque, electric motors for individually driving the driving wheels, and torque control devices for separately controlling the electric motors, the computation circuit comprising means for:
   (a) causing, at least at one of the driving wheels, a temporary increase in driving torque, from its current driving torque, a predetermined guantity beyond that of the other driving wheels, wherein the predetermined quantity is selected from the group consisting of a predetermined fixed amount and a predetermined percentage of the current driving torque of this driving wheel,
   (b) determining a speed differential by comparing speed information determined from the driving wheel with increased driving torque by its respective speed sensor with the speed information determined from at least one of the other driving wheels, which have a relatively lower driving torque, by its respective speed sensor for the purpose of detecting slip,
   (c) performing a step, when the computation circuit determines the speed differential does not exceed a given permissible relative speed differential, wherein a wheel grip limit is not exceeded, selected from the group consisting of (i) transmitting a signal with the information that the temporarily increased driving torque is not critical and (ii) causing the driving torque to be increased again by a greater amount,
   (d) transmitting a signal representing the critical driving torque when the given permissible relative speed differential is determined by the computation circuit, and
   (e) determining the critical driving torque, when the computation circuit determines the speed differential exceeds the given permissible relative speed differential, wherein the wheel grip limit is exceeded, and transmitting the critical driving torque as a signal for the purpose of an iterative approximation to the permissible relative speed differential by repeated temporary increases in the driving torque wherein at least the first of the repeated increases is smaller than its respectively preceding temporary increase in the driving torque.

2. The apparatus according to claim 1, wherein the computation circuit keeps the sum of all driving torques of the motor vehicle at a predetermined value via the torque control device during the temporary increase in the driving torque of at least one driving wheel.

3. The apparatus according to claim 1, wherein the computation circuit varies the ratio of the sum of the driving torques of the driven wheels of a front axle of the motor vehicle to the sum of the driving torques of the driven wheels of a rear axle via the torque control devices.

4. The apparatus according to claim 1, wherein the computation circuit alternately increases the driving torques of at least two of the driven wheels via the torque control devices.

5. The apparatus according to claim 1, wherein the amount of increase in the driving torque of at least one driving wheel is at most a fourth of the current driving torque of this driving wheel.

6. The apparatus according to claim 1, wherein the temporary increase in the driving torque is limited to the time required for less than half a revolution of the wheel having the temporary increase.

7. The apparatus according to claim 1, wherein the permissible relative speed differential lies in the range of 10% to 15%.

8. The apparatus according to claim 1, further comprising wheel load sensors for detecting the magnitude of the wheel load acting at a given moment on the driving wheel whose driving torque has temporarily been increased, and the computation circuit determines information representing the coefficient of friction between this driving wheel and a road in contact with this driving wheel, based on the wheel load and the critical driving torque of this driving wheel.

9. The apparatus according to claim 1, further comprising a warning device, wherein the computation circuit controls the warning device.

10. The apparatus according to claim 1, wherein the computation circuit controls a regulating device selected from at least one member of the group consisting of an antilock braking system and a drive slip regulating system.

11. The apparatus according to claim 1, wherein the computation circuit repeats determining the critical driving torque at predetermined time intervals.

12. The apparatus according to claim 1, wherein by monitoring the speeds of all driving wheels during driving operation, the computation circuit senses sudden changes in slippage at the driving wheels of a front axle and, after a delay, also at the driving wheels of a rear axle of the motor vehicle, whereupon the computation circuit proceeds to determine the critical driving torque.

13. The apparatus according to claim 1, wherein each speed sensor is respectively a component part of one of the electric motors, wherein the electric motors are constructed as permanently excited multipolar motors with electronic commutation, and the torque is determined computationally based on the electrical power supplied to the electric motor of the driving wheel with increased driving torque and on the speed of this driving wheel.

14. The apparatus according to claim 1, wherein two of the driving wheels are arranged on the same longitudinal side of the motor vehicle and the speeds of these two driving wheels are used to determine the relative speed differential between the speeds of two of the driving wheels.

15. The apparatus according to claim 1, wherein a sensor device is provided for determining and transmitting data when the motor vehicle is cornering and, on the basis of the transmitted data concerning the cornering, the computation circuit compensates for the misleading influence due to different radii of curvature of the tracks of the driving wheels to be compared when determining the relative difference in speed.

16. The apparatus according to claim 1, wherein a sensor device is provided for determining when the motor vehicle is cornering and prevents the determination of the critical driving torque during such cornering.

17. The apparatus according to claim 1, wherein the temporary increase is limited to the time required for less than a tenth a revolution of the wheel having the temporary increase.

18. The apparatus according to claim 9, wherein the warning device is a display for displaying a number of different road states.

* * * * *

UNITED STATES PATENT AND TRADEMARK OFFICE
CERTIFICATE OF CORRECTION

PATENT NO. : 5,419,624

DATED : May 30, 1995

INVENTOR(S) : Uwe Adler, et al.

It is certified that error appears in the above-identified patent and that said Letters Patent is hereby corrected as shown below:

Title page,
After "[21]" please insert the following:

```
[22]  PCT Filed:       22 Oct 92

[86]  PCT No.:         PCT/DE90/00908
      §371 Date:       23 Jun 94
      §102(e) Date:    23 Jun 94

[87]  PCT Pub. No.:    WO 93/08049
      PCT Pub. Date:   29 Apr 93
```

Signed and Sealed this

Twenty-fourth Day of October, 1995

Attest:

BRUCE LEHMAN

Attesting Officer

Commissioner of Patents and Trademarks